United States Patent
Beyer et al.

(10) Patent No.: US 9,415,339 B2
(45) Date of Patent: Aug. 16, 2016

(54) PARTICLE COLLECTION DEVICE

(75) Inventors: Geoff Beyer, Mississauga (CA); Simon Feldberg, Mississauga (CA); Clifford Lansil, Mississauga (CA); Mark Lekhter, Mississauga (CA); Vladimir Rasper, Mississauga (CA)

(73) Assignee: SMITHS DETECTION MONTREAL INC. (CA)

( * ) Notice: Subject to any disclaimer, the term of this patent is extended or adjusted under 35 U.S.C. 154(b) by 1073 days.

(21) Appl. No.: 13/378,903

(22) PCT Filed: Jun. 17, 2010

(86) PCT No.: PCT/US2010/039019
§ 371 (c)(1),
(2), (4) Date: Dec. 16, 2011

(87) PCT Pub. No.: WO2010/148217
PCT Pub. Date: Dec. 23, 2010

(65) Prior Publication Data
US 2012/0090285 A1   Apr. 19, 2012

Related U.S. Application Data

(60) Provisional application No. 61/187,961, filed on Jun. 17, 2009.

(51) Int. Cl.
*B01D 46/10* (2006.01)
*H02G 5/00* (2006.01)
*B01D 46/00* (2006.01)

(52) U.S. Cl.
CPC ............ *B01D 46/10* (2013.01); *B01D 46/0005* (2013.01); *B01D 46/0063* (2013.01); *H02G 5/00* (2013.01)

(58) Field of Classification Search
CPC ................................................ G01N 2001/022
See application file for complete search history.

(56) References Cited

U.S. PATENT DOCUMENTS 3,575,405 A * 4/1971 Harding ...................... 269/258
5,854,431 A   12/1998 Linker et al.
(Continued)

FOREIGN PATENT DOCUMENTS

CN   1428801 A   7/2003
EP   0 905 501 A2   3/1999
(Continued)

OTHER PUBLICATIONS

Bekaert. Sintered metal fiber filtration media. Web Access Jun. 11, 2014 provided by https://web.archive.org.<http://www.bekaert.com/en/Product%20Catalog/Products/S/Sintered%20Metal%20Fiber%20filtration%20media.aspx>. pp. 1-3.*
Search Report and Written Opinion mailed Oct. 7, 2010 in Int'l Appln No. PCT/US2010/039019.
(Continued)

*Primary Examiner* — Duane Smith
*Assistant Examiner* — Sonji Turner
(74) *Attorney, Agent, or Firm* — Foley & Lardner LLP

(57) ABSTRACT

A cartridge assembly includes a body portion (14), that is thermally and electrically non-conductive, defining an opening (28), a bus bar (18) coupled to the body portion, the bus bar being thermally and electrically conductive, and a clamping bar (20), including a scalloped surface configured to oppose the bus bar, the clamping bar being thermally and electrically conductive. At least one of the bus bar and the clamping bar is biased toward the other of the bus bar and the clamping bar.

12 Claims, 3 Drawing Sheets

(56) References Cited

U.S. PATENT DOCUMENTS

| | | | | |
|---|---|---|---|---|
| RE38,797 E | * | 9/2005 | Linker | G01N 1/2273 73/863.12 |
| 6,978,657 B1 | * | 12/2005 | Baumann | G01N 1/2214 73/28.04 |
| 7,299,711 B1 | * | 11/2007 | Linker | G01N 1/2214 73/863.23 |
| 2010/0130796 A1 | * | 5/2010 | Combes | G01N 1/405 568/935 |

FOREIGN PATENT DOCUMENTS

| | | | | |
|---|---|---|---|---|
| GB | WO 2009001065 A1 | * | 12/2008 | G01N 1/405 |
| GB | WO 2009001070 A1 | * | 12/2008 | G01N 1/405 |
| WO | WO-00/63669 A1 | | 10/2000 | |

OTHER PUBLICATIONS

Chinese Office Action dated Feb. 8, 2014 issued in Chinese Application No. 201080034187.7.

* cited by examiner

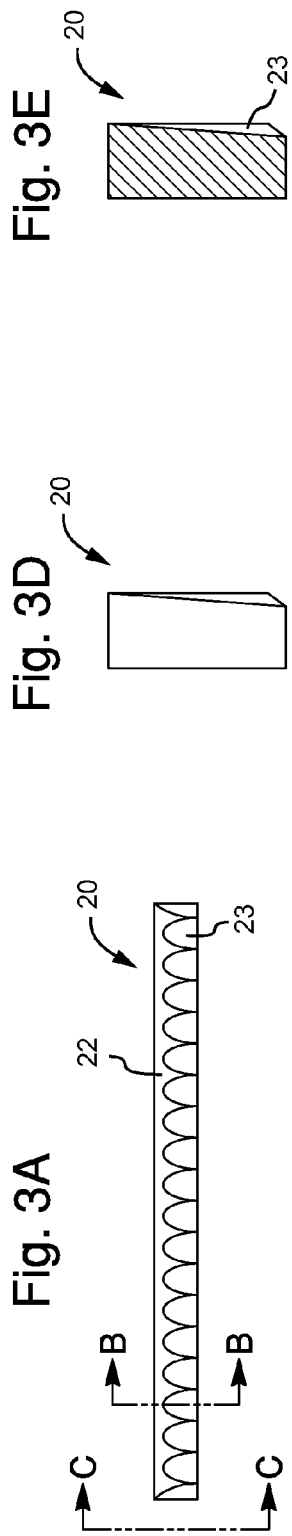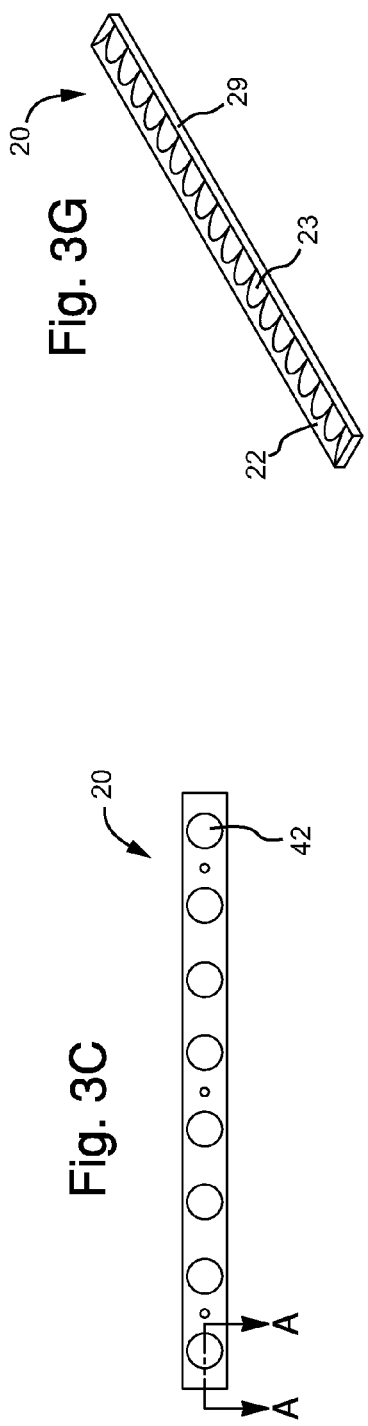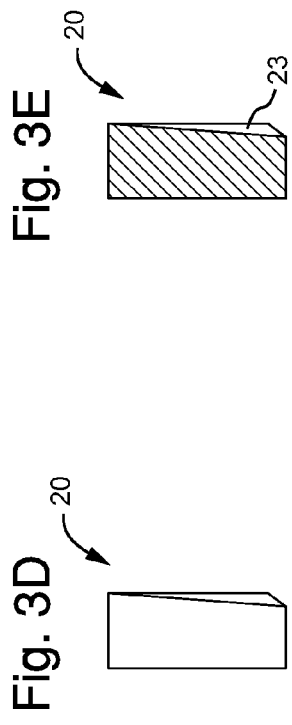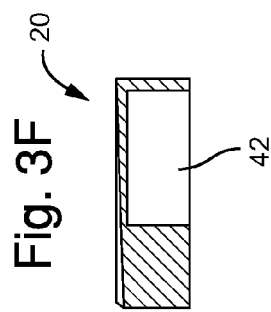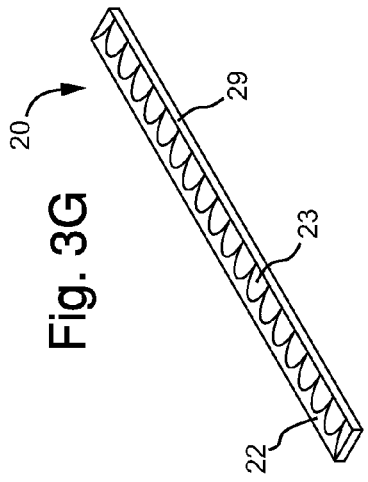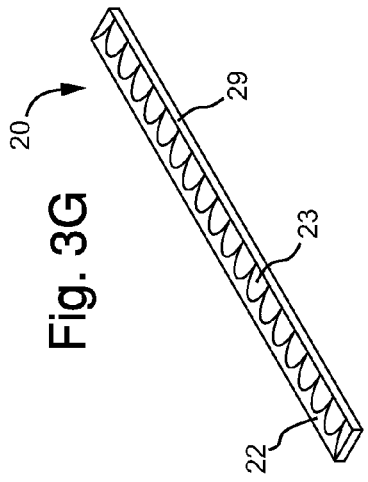

PARTICLE COLLECTION DEVICE

CROSS-REFERENCE TO RELATED PATENT APPLICATIONS

This application claims the benefit of priority of U.S. Provisional Application No. 61/187,961, filed Jun. 17, 2009, the complete disclosure of which is incorporated by reference herein.

BACKGROUND

The present disclosure relates generally to the field of particle collection devices, and more specifically, to particle collection and similar devices used to screen objects.

Screening for explosive materials and illegal narcotics is now routine in airports, train stations, sports arenas, and other locations charged with handling large volumes of individuals. Often, individuals and their belongings must be screened for explosive materials and/or explosive residues. While it is desirable to identify individuals carrying illegal narcotics, it is also important from a security standpoint, to screen individuals for the presence of explosive materials.

SUMMARY

One embodiment relates to a cartridge assembly comprising a body portion, that is thermally and electrically non-conductive, defining an opening; a bus bar coupled to the body portion, the bus bar being thermally and electrically conductive; and a clamping bar, including a scalloped surface configured to oppose the bus bar, the clamping bar being thermally and electrically conductive; wherein at least one of the bus bar and the clamping bar is biased toward the other of the bus bar or the clamping bar.

Another embodiment relates to a preconcentrator comprising a body portion, configured to be disposed in an airflow, the body portion defining an opening through which at least a portion of the airflow is directed; an other body portion defining an opening that is configured to align with the opening in the body portion when the other body portion is secured to the body portion; a clamping bar, mounted to at least one of the body portion or the other body portion, the clamping bar comprising a scalloped surface configured to at least partially secure a mesh between the body portion and the other body portion, the clamping bar being formed of a material that is thermally and electrically conductive; and means for securing the body portion and the other body portion one to another.

Yet another embodiment relates to a screening device comprising a source configured to generate a flow of air through which an object is to pass; a particle collection device, disposed in a path of the flow, the particle collection device being configured to capture particulate matter dislodged from the object by the flow, the particle collection device comprising a body portion defining an opening through which at least a portion of the flow is to pass; an other body portion defining an opening that aligns with the opening in the body portion when the other body portion is secured to the body portion; and a clamping bar, formed of a material that is conductive, comprising a scalloped surface that is configured to secure a mesh that is disposed between scalloped surface and at least one of the body portion or the other body portion.

Yet another embodiment relates to a device comprising a body portion and an other body portion respectively defining an aperture when the body portion and the other body portion are in a secured orientation; and a clamping bar, mounted to one of the body portion and the other body portion, the clamping bar being biased toward that body portion that opposes a scalloped surface included on the clamping bar, wherein at least a portion of the scalloped surface is configured to make physical contact with a mesh that extends across said apertures when the body portion and the other body portion are in the secured orientation.

BRIEF DESCRIPTION OF THE DRAWINGS

FIG. 3A is top view of a clamping bar according to an exemplary embodiment.

FIG. 3B is a front view of the clamping bar of FIG. 3A according to an exemplary embodiment.

FIG. 3C is a bottom view of the clamping bar of FIG. 3A according to an exemplary embodiment.

FIG. 3D is a side view of the clamping bar of FIG. 3A taken along line C-C according to an exemplary embodiment.

FIG. 3E is a cross-sectional view of the clamping bar of FIG. 3A taken along line B-B according to an exemplary embodiment.

FIG. 3F is a cross-sectional view of the clamping bar of FIG. 3A taken along line A-A according to an exemplary embodiment.

FIG. 3G is a perspective view of the clamping bar of FIG. 3A according to an exemplary embodiment.

DETAILED DESCRIPTION OF EXEMPLARY EMBODIMENTS

Figure 1:
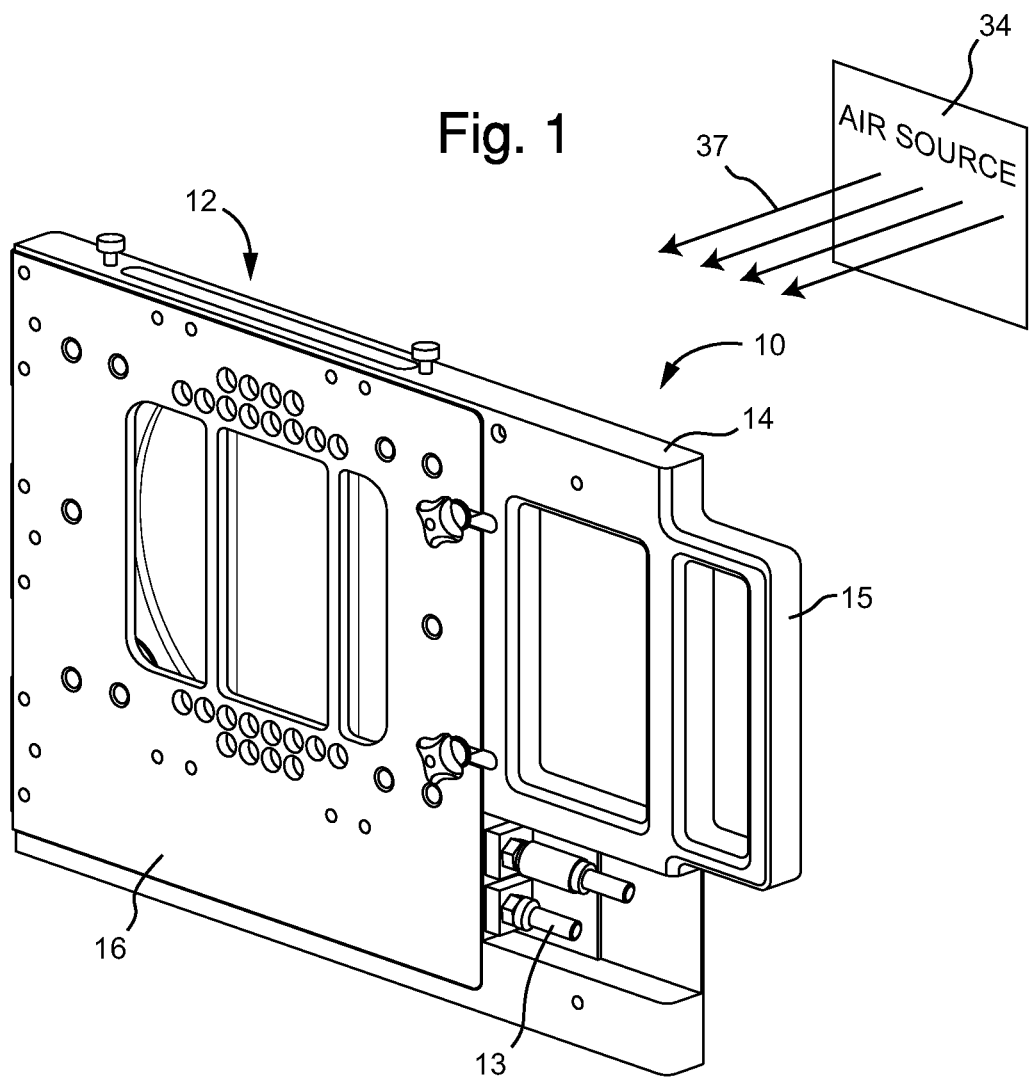
FIG. 1 illustrates a particle collection device according to an exemplary embodiment.

Referring to FIG. 1, a particle collection device 10 (e.g., a cartridge assembly, a mesh cartridge assembly, a preconcentrator, etc.) is shown according to an exemplary embodiment. Particle collection device 10 includes a body 12 having a first portion or housing 14 (e.g., a body portion, a first body portion, a housing, etc.) and a second portion or door 16 (e.g., an other body portion, a second body portion, a door or door assembly, etc.). One or more disconnect members 13 may be provided to provide electrical connectivity between particle collection device 10 and other components. Device 10 may include a handle 15 configured to facilitate the insertion and/or removal of device 10 from another component, such as a screening device, etc. For example, device 10 may be a preconcentrator that is used to capture particles, such as particles of narcotics and/or explosive materials, blown off a human passing through a security screening device.

According to embodiments, device 10 is configured to be placed in the path of an airflow and capture particles travelling within the airflow. The particle collection device can be used in any suitable instrument or configuration, such as, for example, in walk-through detection equipment (e.g. portals) at security or customs checkpoints. For example, device 10 may utilized as part of a screening device (e.g., a portal, etc.) such that air is directed along an air flow 37 from an air source 34 over and/or past an object (e.g., a person, luggage, etc.) and passes through device 10. Device 10 captures particles travelling with the air passing along air flow 37 through device 10. Upon being captured by device 10, the particles may be subjected to further analysis (e.g., analysis by a device such as an ion mobility spectrometry (IMS) device, a Fourier transform infrared spectroscopy (FTIR) device, and the like).

Figure 2:
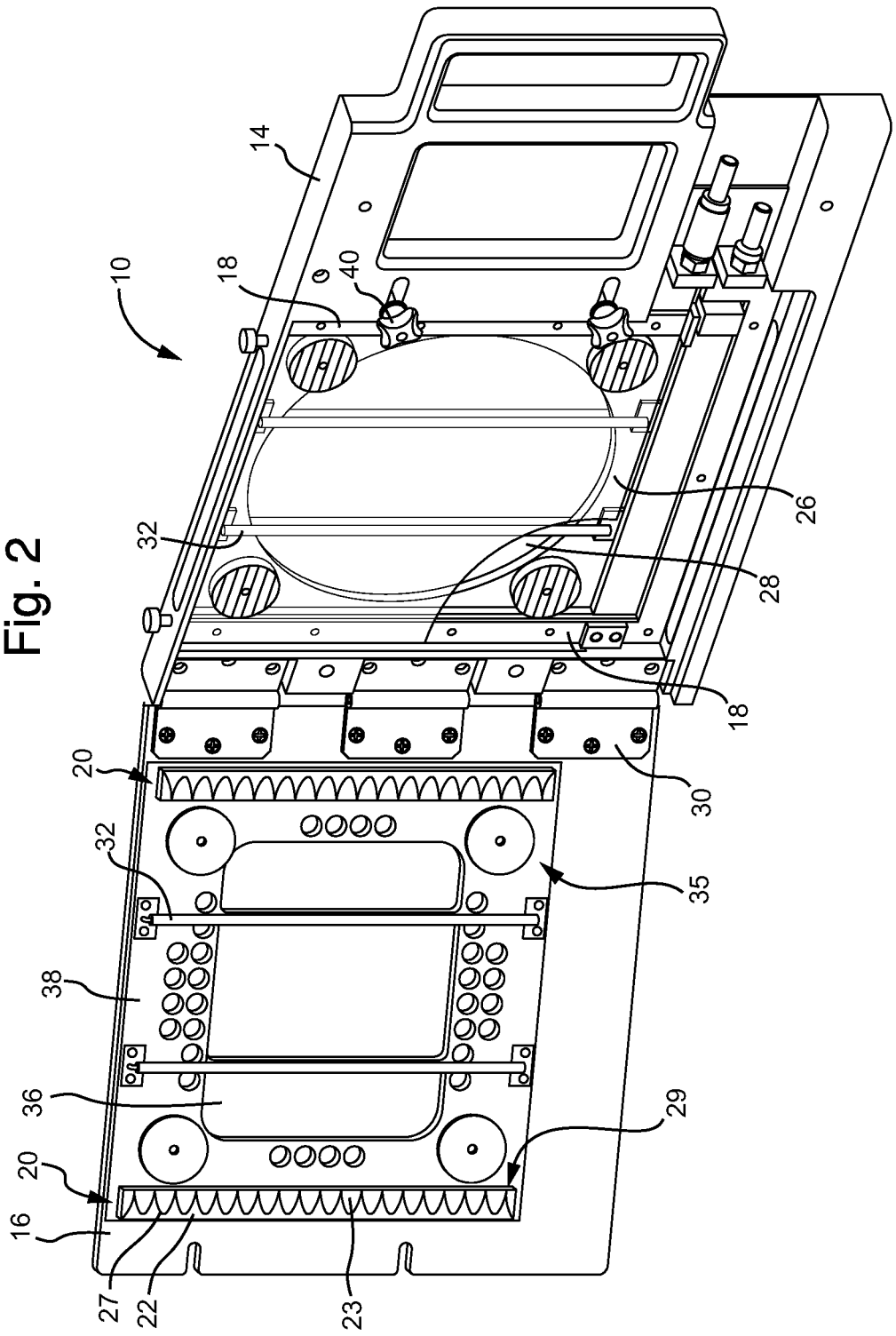
FIG. 2 illustrates the particle collection device of FIG. 1 in an open configuration according to an exemplary embodiment.

Referring to FIG. 2, device 10 is shown in greater detail in accordance with various embodiments. As shown in FIG. 2, housing 14 and door 16 may be pivotally coupled to one another. For example, one or more hinges 30 may be utilized to couple housing 14 and door 16. Alternatively, housing 14 and door 16 may be pivotally coupled without the use of a hinge (e.g., by using one or more "pseudo-hinge" features, pivot rods, or components). According to yet another embodiment, housing 14 and door 16 may be completely separable and may be coupled utilizing a snap fit, interference fit, or other type of mechanical or other coupling method.

Referring further to FIG. 2, housing 14 defines an aperture 28 that permits air to flow through device 10. According to an embodiment, housing 14 is a generally planar member, while in other embodiments housing 14 may have a curved (e.g., concave, convex, etc.) profile with an apex extending toward or away from door 16. Although aperture 28 is shown as being generally circular in shape, any suitable shape or configuration (e.g., square, rectangular, etc.) may be used in connection with aperture 28. One or more bus bars 18 (electrically and/or thermally conductive members, etc.) may be coupled or otherwise supported by housing 14. In other embodiments, one bus bar 18 is provided to each of two opposite portions of aperture 28. While bus bars 18 are shown as being generally straight, elongated members, other configurations (e.g., curved, irregularly-shaped, etc.) of bus bars may be used, and more or less bus bars than those shown in FIG. 2 may be utilized.

Door 16 defines an aperture 36 that permits air passing through aperture 28 to completely pass through device 10. In one embodiment, apertures 28, 36 are generally aligned when device 10 is in a closed or secured position (as shown in FIG. 1). As shown in FIG. 2, aperture 36 may have a generally rectangular shape, while in other embodiments aperture 36 may take other shapes and/or configurations (e.g., circular, square, etc.). Both of apertures 28, 36 may be sized appropriately to permit for the appropriate airflow through device 10. According to one embodiment, door 16 may have a curved (e.g., concave, convex, etc.) profile having an apex extending either toward or away from housing 14. One or both of housing 14 and door 16 may include one or more supports 32 configured to provide additional support to the components of device 10.

In embodiments, device 10 may further comprise a mesh 26 (e.g., a stainless-steel mesh material or assembly, a filter, screen, wire mesh, etc.). Mesh 26 may be placed in the path of the airflow travelling through device 10 and be configured to collect particles with traces of target compounds, including but not limited to, narcotic or explosive substances. For example, mesh 26 is sized to capture particles of the size of narcotic or explosive particles expected to cling to objects. After the collection of particles is accomplished, heat can be applied to mesh 26 to release, e.g., liberate, captured particles, and the resulting vapors can be analyzed using any suitable method, such as, for example ion mobility spectrometry (IMS). As shown in FIG. 2, mesh 26 may be generally square in shape. According to various other embodiments, mesh 26 may be any suitable type and take any suitable shape (e.g., a shape suitable to cover apertures 28, 36, circular, rectangular, etc.). The mesh material may be electrically and/or thermally conductive to facilitate heating of mesh 26, e.g., act as a resistor). For example, a stainless steel mesh is used to capture particles blown off a human at least partially positioned in the air flow. Furthermore, mesh 26 may be a removeable/replaceable component of device 10.

Door 16 may further include one or more clamping bars 20 (e.g., clamping members, bus bars, etc.). In one embodiment, clamping bars 20 and bus bars 18 generally face one another when door 16 is closed such that mesh 26 is secured between clamping bars 20 and bus bars 18. Clamping bars 20 and/or bus bars 18 may be in electrical and/or thermal contact with mesh 26. One or more of bus bars 18 and/or clamping bars 20 may be biased toward the other (e.g., via a spring, a curvature in the component profile, etc.) to further increase the retention force on mesh 26. Furthermore, the relative positions of bus bars 18 and clamping bars 20 may be reversed in some embodiments. In some embodiments, bus bars 18 and clamping bars 20 are configured to retain mesh 26 so all, or at least a portion of, mesh 26 remains substantially planar as air passes through mesh 26. In additional embodiments, an insert 38 (e.g., a thermal insert, an electrically and/or thermally insulating member, etc.) may be provided as part of door 16 and may electrically and/or thermally insulate clamping bars 20 from the remainder of door 16.

Clamping bars 20 can be generally flat, or alternatively may include a surface 22 designed to hold mesh 26 more effectively. In embodiments, surface 22 can have scalloped notches 23 (e.g., scallops, notches, recesses, etc.) along the length of clamping bar 20. Scalloped notches 23 can improve one or more of electrical, mechanical, or thermal contact between mesh 26 and clamping bars 20 and/or bus bars 18. For example, mesh 26 may contact a primary portion of surface 22 while not contacting the recessed portion of a scallop. As shown in FIG. 2, the transition between the portion of mesh 26 sandwiched between bus bars 18 and clamping bars 20 and the unsupported portion of mesh 26 can occur along a line 27 that follows a machined scalloped profile of clamping bars 20, thus increasing the length of transition line 27 (relative to a generally straight transition line). For example, transition line 27 can be more than two times longer than a straight transition line on the same clamping bar. Scallops 23 provide depth to the transition phenomenon that is defined by the distance from the crest of each scallop 23 to a front edge or surface 29 of each clamping bar 20. The ends of the scalloped notches 23 can be increased to decrease the amount of contact between the edge of mesh 26 and clamping bars 20 and/or bus bars 18. Deeper ended scalloped notches also reduce contact of mesh 26 with bus bars 18, in turn minimizing heat or electronic damage that may otherwise may occur to mesh 26. For example, overheating of mesh 26 (e.g., a stainless steel mesh) may result in deformation of mesh and/or the mesh coming apart. In some embodiments, clamping bar 20 may have intermittent (e.g., non-continuous, etc.) electrical contact with mesh 26.

Device 10 may include one or more clamping assemblies, shown in FIG. 2 as clamping knobs 40 (e.g., clamps, fasteners, etc.). Clamping knobs 40 can provide additional support for mesh 26 as it resists an airflow, including intermittent airflow that can permeate the mesh material. Clamping knobs 40 may be configured to secure surface 22 of clamping bar 20 and/or a surface of bus bar 18 into contact with mesh 26 disposed between clamping bars 20 and bus bars 18. Clamping knobs 40 can be made of any suitable material.

In one embodiment, device 10 further includes one or more deflection limiters, shown in FIG. 2 as support disks 35. Support disks 35 provide additional support for mesh 26 as the support disk may resist airflow and limit deflection of the mesh 26 due to pressure from the airflow 37 and/or from thermal expansion of the mesh 26 during heating, particularly near the clamping edge, where the mesh may be vulnerable to damage. Support disks 35 can be attached to either or both the housing 14 and the door 16 and can be of various shape, though in the illustrated embodiment they are round. In an embodiment, the support disks 35 are formed of an electrically non-conducting material, but may be of either a thermally conducting or thermally non-conducting material.

Referring to FIGS. 3A-G, clamping bar 20 is shown in greater detail according to an exemplary embodiment. For example, clamping bar 20 may include scallops 23 (e.g., notches, recesses, grooves, indents, etc.). Respective scallops may have a generally curved profile extending along a surface 22 of clamping bar 20. In other embodiments, scallops 23 are formed by a cylindrical machining tool (not shown) such that the tool rotates and forms the curved surface of the scallop. As such, the size, shape, and depth of the scallops can be controlled by adjusting the depth of cut and/or angle of the tool. In embodiments, one or more generally cylindrically-shaped recesses 42 are provided in a bottom surface of clamping bar 20. Any number of recesses 42 may be utilized, and the recesses may take any suitable size and/or shape. In one embodiment, similarly-sized scallops 23 are provided adjacent to one another in a generally continuous manner along the length of clamping bar 20. In other embodiments, scallops 23 are spaced apart along clamping bar 20 and/or the individual scallops may take varying shapes/sizes along the length of clamping bar 20. Other forms and/or configurations besides scallops may be used according to various alternative embodiments, including, but not limited to, straight-edged recesses, flat/curved-bottomed notches, wavy-shaped structures, and the like.

It should be noted that mesh testing has shown that the edges of the mesh may be more vulnerable when a crease is formed in the edge area, in which case the mesh material may start to burn at a much faster rate than creases situated in the central part of the mesh. Poor or no contact of the material, that forms the mesh, with bus bars near the edges of the mesh results in low current density in that area, with less tendency to burn if a crease is formed starting from the edge (in most instances the edge crease is formed close to bus bar). Thus, the scalloped configuration of the clamping bars may decrease the tendency of the mesh material to burn in the edge areas.

It should further be noted that there may be an additional benefit from using a square-shaped mesh. The mesh is most prone to failure along the clamping area close to the bus bars. In some instances, failure may occur gradually within approximately 8,000-20,000 samples because the mesh may be frequently removed from cartridge for cleaning during this time (approximately every 1,000-2,000 samples). A rectangular mesh restricts its installation orientation into the cartridge, while a square mesh allows placement into the cartridge on either side (e.g., multiple orientations) in such a way that the sides of the mesh with the least damage can be made to contact the bus bars while more damaged sections can directed in the path of power transfer. Thus, a square-shaped mesh may prolong the useful life of the mesh.

For purposes of this disclosure, the term "coupled" refers to the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate member being attached to one another. Such joining may be permanent in nature or alternatively may be removable or releasable in nature. Such joining may also relate to mechanical, fluid, or electrical relationship between the two components.

It is important to note that the construction and arrangement of the elements of particle collection device as shown in the exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, materials, colors, orientations, etc.) without materially departing from the novel teachings and advantages of the subject matter recited in the embodiments. Accordingly, all such modifications are intended to be included within the scope of the present disclosure as defined in the appended claims. The order or sequence of any process or method steps may be varied or re-sequenced according to alternative embodiments. Other substitutions, modifications, changes, and/or omissions may be made in the design, operating conditions, and arrangement of the exemplary embodiments without departing from the spirit of the present disclosure.

What is claimed is:

1. A preconcentrator comprising:
   a first body portion configured to be disposed in an airflow, the first body portion defining a first opening through which at least a portion of the airflow is directed;
   a second body portion defining a second opening that is configured to align with the first opening when the second body portion is secured to the first body portion;
   a clamping bar mounted to at least one of the first body portion and the second body portion, the clamping bar comprising a scalloped surface configured to at least partially secure a mesh between the first body portion and the second body portion, the clamping bar being formed of a material that is thermally and electrically conductive; and
   means for securing the first body portion and the second body portion one to another.

2. The preconcentrator of claim 1, wherein the scalloped surface of the clamping bar is in one or more of thermal and electrical contact with the mesh when the first body portion and the second body portion are secured one to another.

3. The preconcentrator of claim 2, wherein at least a portion of the mesh adjacent to the clamping bar is substantially planar.

4. The preconcentrator of claim 1, wherein the mesh is configured to capture particulate matter in the airflow.

5. The preconcentrator of claim 1, wherein the preconcentrator is configured to receive the airflow from a portal.

6. The preconcentrator of claim 1, wherein the preconcentrator is configured to heat the mesh to liberate particles captured from the airflow by the mesh.

7. The preconcentrator of claim 1, wherein the means for securing comprises a clamping assembly.

8. The preconcentrator of claim 1, wherein the first body portion and the second body portion are hinged one to another.

9. The preconcentrator of claim 1, wherein the mesh comprises a wire mesh.

10. The preconcentrator of claim 1, wherein the scalloped surface of the clamping bar is not in continuous electrical contact with the mesh when the second body portion is secured to the first body portion.

11. The preconcentrator of claim 1, wherein the second body portion has a curved profile in which an apex of the curved profile is directed toward the first body portion.

12. The preconcentrator of claim 1, further comprising means for biasing the scalloped surface of the clamping bar toward one or more of the first body portion and the second body portion that opposes that first body portion to which the clamping bar is mounted.

* * * * *